United States Patent
Goebel et al.

(10) Patent No.: US 6,347,711 B1
(45) Date of Patent: *Feb. 19, 2002

(54) FILTER FOR MEDICAL FLUIDS

(75) Inventors: Udo Goebel, Melsungen-Kirchhof; Manfred Friederichs, Melsungen; Volker Harms, Kassel; Manfred Heitmann, Haan; Tabea Hinkel, Melsungen; Karl-Heinz Koch, Melsungen; Hans-Joachim Otto, Melsungen; Klaus Siemon, Koerle; Martin Sippel, Melsungen, all of (DE)

(73) Assignee: B. Braun Melsungen AG, Melsungun (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/340,153

(22) Filed: Jun. 28, 1999

(30) Foreign Application Priority Data

Jun. 27, 1998 (DE) ................................. 298 11 529 U

(51) Int. Cl.⁷ ............................................. B01D 63/00
(52) U.S. Cl. ................................. 210/436; 210/472
(58) Field of Search ................................. 210/436, 472

(56) References Cited

U.S. PATENT DOCUMENTS

| | | | |
|---|---|---|---|
| 4,294,594 A | | 10/1981 | Sloane, Jr. et al. |
| 4,341,538 A | * | 7/1982 | Vadney et al. |
| 4,906,260 A | * | 3/1990 | Emheiser et al. |
| 5,348,646 A | * | 9/1994 | Costello, Jr. et al. |

FOREIGN PATENT DOCUMENTS

EP 0302722 8/1988

* cited by examiner

Primary Examiner—John Kim
Assistant Examiner—David Sorkin
(74) Attorney, Agent, or Firm—Diller, Ramik & Wight

(57) ABSTRACT

A filter for medical fluids comprises a hydrophilic membrane (18) dividing the filter into an inlet chamber (20) and an outlet chamber (22). This prevents air from penetrating the outlet chamber (22). The air retained in the inlet chamber (20) is discharged through vent holes (30, 32). Each vent hole (30, 32) is covered with a hydrophobic membrane (34, 36). According to the invention one of the vent holes (30) is provided in a front wall (38) opposite the hydrophilic membrane (18). The other vent hole (32) is provided in a rear wall (46) located opposite the front wall (38) so that the two vent holes (30, 32) point in opposite directions. Owing to this arrangement of the two vent holes (30, 32) one vent hole (30, 32) points upwards irrespective of the filter position. This improves venting of the inlet chamber (20).

16 Claims, 2 Drawing Sheets

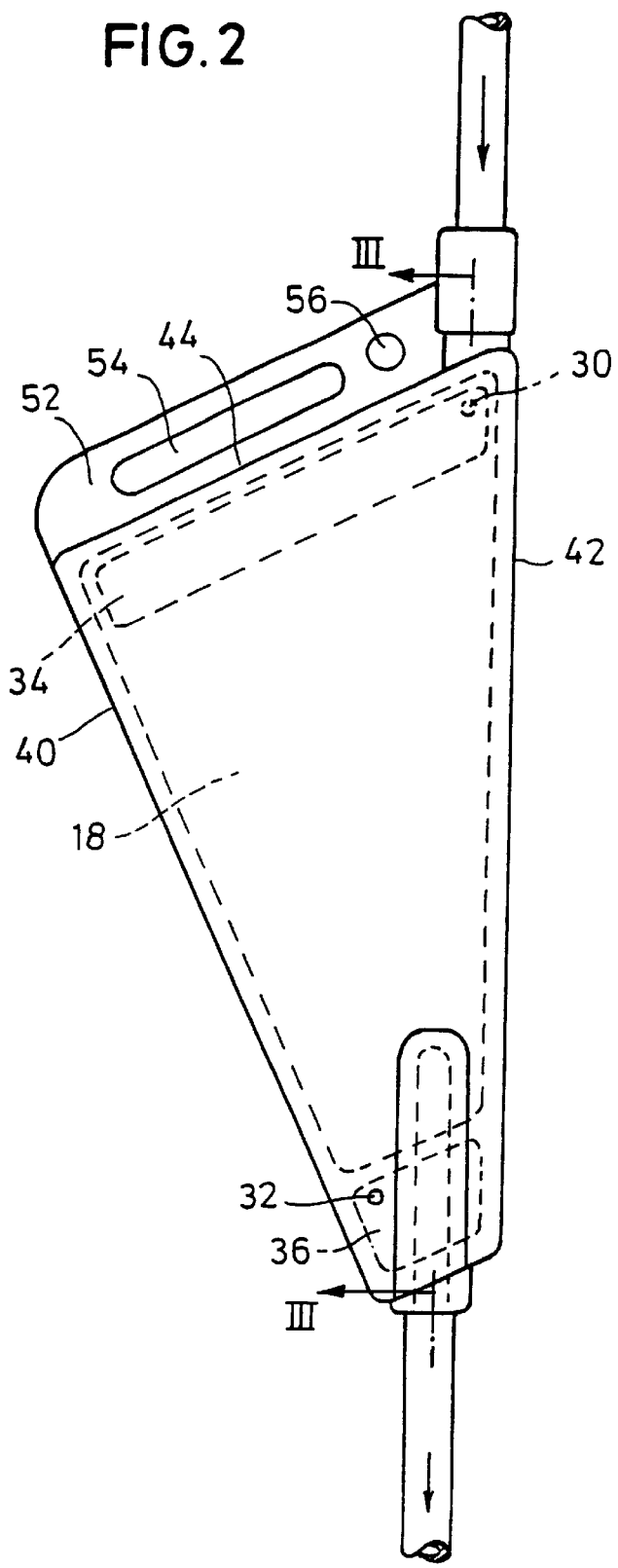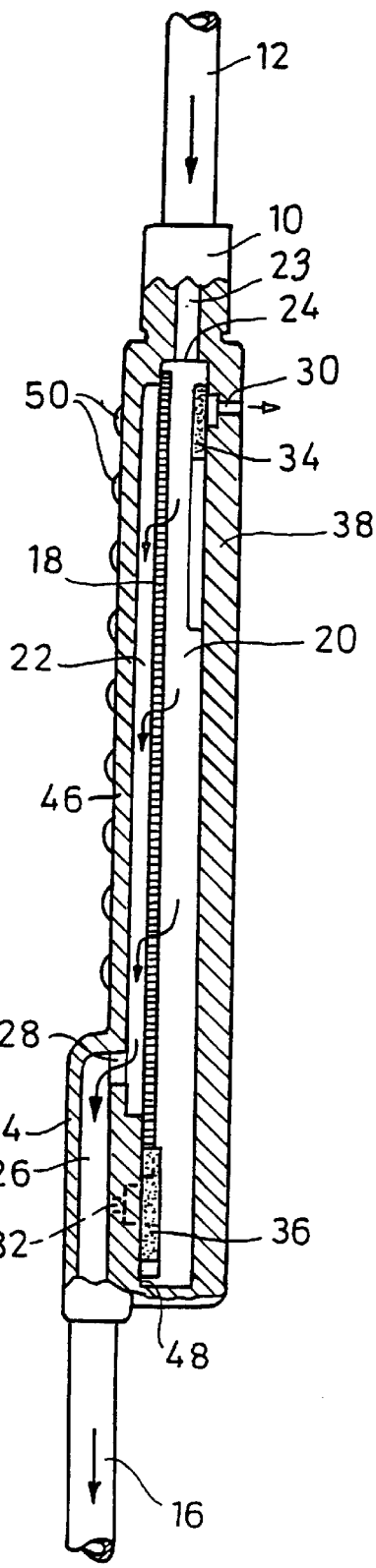

FILTER FOR MEDICAL FLUIDS

BACKGROUND OF THE INVENTION

The invention relates to a filter for medical fluids, in particular fluids intravenously administered to the patient.

It must be ensured that medical fluids administered to a patient do not contain air or other gases. To remove the air from the medical fluid filters with a hydrophilic and a hydrophobic membrane are used. When hydrophilic membranes have been wetted with the fluid they are fluid-permeable and air-impermeable up to a limiting pressure. Hydrophobic membranes are always air-permeable and fluid-impermeable.

Such a filter is, for example, described in EP 0 302 722 B1. The filter comprises a flat housing divided by the hydrophilic membrane, which in the case of the present filter extends over the overall filter cross-section, into an inlet and an outlet chamber. The complete inner wall of the two chambers is formed by the hydrophilic filter membrane. For venting the inlet chamber two vent holes covered with a hydrophobic membrane are arranged opposite the hydrophilic membrane. In vertically arranged filters the two vent holes are provided in an upper and a lower section. To ensure reliable venting of the inlet chamber care must be taken that the filter is always arranged in such a way that the vent holes point upwards.

U.S. Pat. No. 4,294,594 discloses a filter comprising an inlet chamber and an outlet chamber in a housing. Between the two chambers an intermediate chamber separated from the inlet chamber by a deep-bed filter is arranged. The intermediate chamber is separated from the outlet chamber by a hydrophobic filter membrane. At the upper end of both the inlet chamber and the intermediate chamber a vent hole with a hydrophobic membrane is provided. These vent holes are located at that end of the housing which forms the upper end when the filter is properly arranged. However, proper arrangement of the filter cannot always be ensured, in particular when the filter is attached to the patient's lower arm since the lower arm can, of course, assume different positions. If air penetrates the infusion system, for example when the filter is upside-down, the air does not leave the housing when the filter has been wetted.

SUMMARY OF THE INVENTION

It is the object of the present invention to create a filter for medical fluids with reliable venting.

The filter according to the present invention has at least two vent holes, both covered with a hydrophobic membrane, one of which is arranged in a front wall opposite the hydrophilic membrane and the other in the rear wall. Thus the vent holes are provided in filter walls arranged opposite each other and at opposite ends of the housing. Since at least two vent holes point in opposite directions, there is always one vent hole pointing upwards irrespective of the horizontal arrangement of the filter. Air or other gases can easily escape through the vent hole pointing upwards, even when the filter is only slightly inclined. It is thus ensured that no air bubbles accumulate in the inlet chamber, which would not escape or escape only very slowly owing to the filter position and would thus affect the flow rate.

In a particularly preferred embodiment of the filter according to the invention at least one hydrophobic membrane extends over almost the overall filter width at the level of the corresponding vent hole, with the filter width possibly varying in the longitudinal extension of the filter. In this way air bubbles are collected by this hydrophobic membrane over the overall filter width at that location and discharged through the vent hole. The hydrophobic membrane extending over the overall filter width can be connected with a plurality of vent holes. Further, the corresponding vent hole can also extend over almost the overall filter width and possibly comprise crossbars to fix the hydrophobic membrane.

In the vertically arranged filter one of the vent holes is preferably arranged in the upper section and another vent hole in the lower section of the inlet chamber. When the filter is used in a vertical infusion tube as is frequently the case, it is thus ensured that during administration of the medical fluid to the patient venting of the inlet chamber is substantially effected through the upper vent hole. When the filter is filled with fluid, venting is essentially effected through the lower vent hole. This allows uniform flow of the fluid into the inlet chamber.

The hole which forms the lower vent hole in the present configuration is preferably the vent hole provided in the rear wall. Thus no hydrophilic membrane is arranged opposite the lower vent hole. This prevents air bubbles from accumulating at the hydrophilic membrane local to the lower vent hole and affecting uniform venting of the inlet chamber in particular when the filter is being filled.

BRIEF DESCRIPTION OF THE DRAWINGS

Hereunder an embodiment of the present invention is explained in detail with reference to the drawings in which

FIG. 2 shows a schematic rear view of the filter shown in FIG. 1; and

FIG. 3 shows a section along line III—III of FIG. 2.

DESCRIPTION OF THE PREFERRED EMBODIMENT

Figure 1:
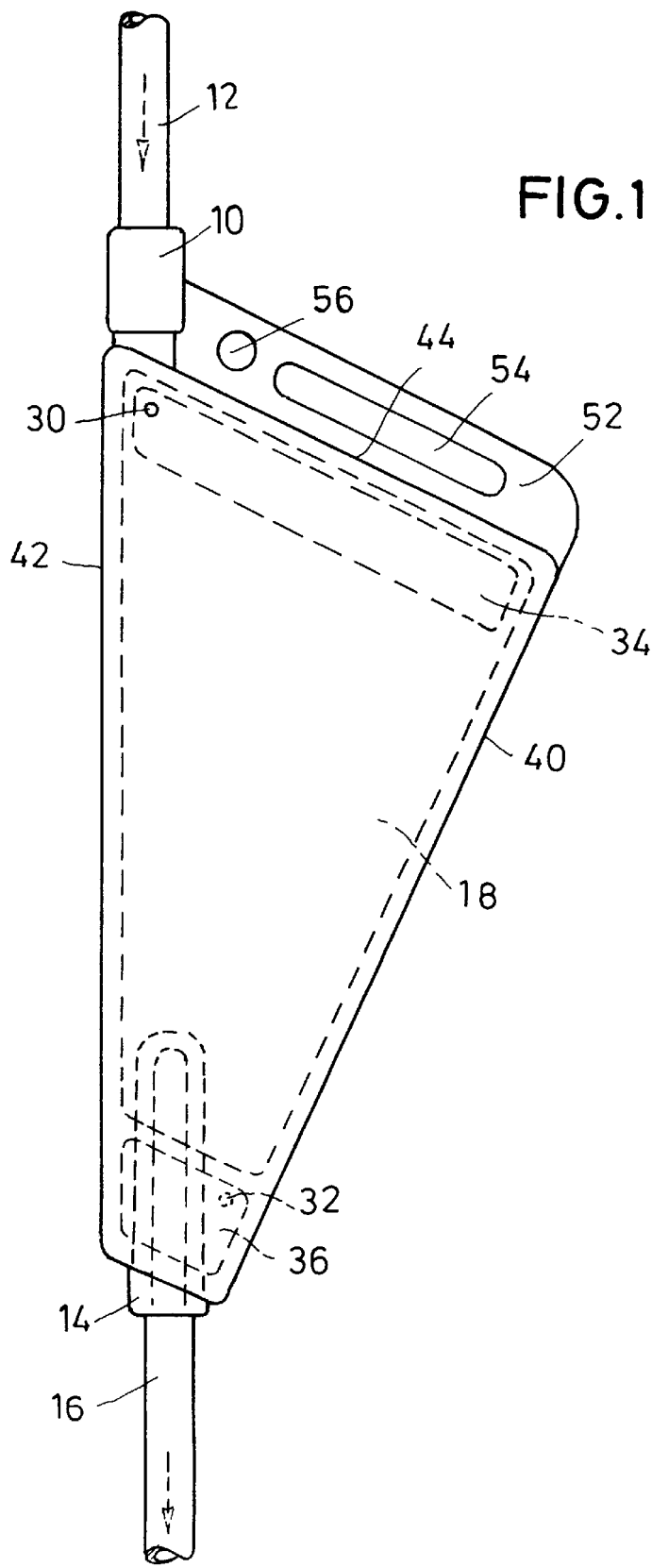
FIG. 1 shows a schematic front view of a preferred embodiment of the filter.

The filter shown in the figures is a flat filter preferably made of transparent material, whose inlet conduit 10 is connected with a tube 12 or provided with a Luer-Lock connector through which medical fluid is supplied to the filter. An outlet conduit 14 is provided with a Luer-Lock connector or connected with a tube 16 which, for example, leads to a cannula inserted in the patient's body.

A hollow space provided in the filter is divided by a hydrophilic membrane 18 into an inlet chamber 20 and an outlet chamber 23. A duct 22 arranged in the inlet conduit 10 is connected with the inlet chamber 20 via an inlet opening 24. Correspondingly a duct 26 arranged in the outlet conduit 14 is connected with the outlet chamber 22 via an outlet opening 28.

To filter medical fluids these fluids are fed through the tube 12 to the inlet chamber 20 of the filter. The hydrophilic membrane filters particles and other foreign matter out of the medical fluid. In addition, the hydrophilic membrane, through which only fluids but no gases can pass, ensures that no air or other gases penetrate the outlet chamber. The filtered and gas-free fluid in the outlet chamber 22 is fed through the outlet opening 28 and the tube 16 into the patient's body.

The air or gases retained by the hydrophilic membrane 18 must be discharged from the inlet chamber 20. For this purpose vent holes 30, 32 are provided in the inlet chamber 20. Each vent hole 30, 32 is closed towards the inlet chamber by means of a hydrophobic membrane 34, 36. In the vertical arrangement of the filter as shown the vent hole 30 is provided in the upper filter section and the vent hole 32 is provided in the lower filter section. The vent hole 30 is arranged in a front wall 38 opposite the hydrophilic membrane 18. Thus the hydrophobic membrane 34 associated with the vent hole 30 is disposed opposite the hydrophilic membrane 18 and is arranged in parallel to the latter. In order to ensure adequate venting in the upper section the hydrophobic membrane 34 extends over almost the overall filter width between the two side edges 40, 42 of the filter (FIG. 2). The hydrophobic membrane 34 extends adjacent to an upper filter edge 44 so that no air can accumulate above the hydrophobe membrane 34 when the filter is substantially vertically arranged. In addition to the vent hole 30 further vent holes can be provided in the front wall 38 at the level of the hydrophobic membrane 34.

The second vent hole 32 provided in the lower filter section (FIG. 2) is located in a rear wall 46 of the filter so that the vent holes 30, 32 point in opposite directions. The rear wall 46 is thicker by the height of the outlet chamber 22 local to the vent hole 32 so that the vent hole 32 is connected with the inlet chamber 20. The hydrophobic membrane 36 closing the vent hole 32 is attached to an inner side 48 of the rear wall 46 and arranged at the same level as the hydrophilic membrane 18 (FIG. 3). Thus the hydrophilic membrane 18 does not extend over the overall filter cross-section. The vent hole 32 is provided laterally next to the outlet conduit 14 (FIG. 2). Analogously to the hydrophobic membrane 34 the hydrophobic membrane 36 also extends over the overall filter width between the two side edges 40, 42. At the level of the hydrophobic membrane 36 further vent holes in addition to the vent hole 32 can be provided in the rear wall 46, which are all covered by the membrane 36.

Moreover, further vent holes covered with a hydrophobic membrane can be provided in the front wall 38, for example, to ensure reliable venting of the inlet chamber 20 when the filter is almost horizontally arranged. Further vent holes can in particular be disposed opposite the vent holes 30, 32. Furthermore, vent holes can be provided in the side walls. Preferably a vent hole is arranged in each corner of the filter so that there is a vent hole at the highest point of the inlet chamber 20 no matter how the filter is arranged. Each vent hole is covered with a hydrophobic membrane.

To ensure in a simple way that the filter is connected in flow direction when the tubes 12, 16 are connected to the inlet conduit 10 or the outlet conduit 14, respectively the outer contour of the filter is of triangular shape with one vertex of the triangle pointing towards the outlet conduit 14. The outer contour of the filter thus looks like an arrowhead pointing in flow direction. In the vertical arrangement shown the outer contour of the filter shown looks like an asymmetrical triangle whose upper edge 44 is inclined and does not extend horizontally. This ensures that air bubbles do not accumulate at the upper edge 44 but always bubble up towards the vent hole 30.

At the rear wall 46 additional supporting lugs 50 are provided which allow air supply to the skin when the filter is placed onto the skin. Such supporting lugs can also be disposed on the outer side of the front wall 38. Instead of supporting lugs supporting ribs can be provided.

A shoulder 52 is connected with the upper edge 44 of the filter. In the shoulder 52 recesses 54, 56 are provided through which a cord or a strip can be led in order to attach the filter to the patient's body or a device.

What is claimed is:

1. A filter for medical fluids comprising:
    a filter housing including first and second ends and opposite walls (38, 46) defining opposite sides of said filter housing,
    a hydrophilic filter (18) between said opposite walls (38, 46),
    a first (38) of said opposite walls (38, 46) and said hydrophilic filter (18) defining an inlet chamber (20),
    a second (46) of said opposite walls (38, 46) and said hydrophilic filter (18) defining an outlet chamber (22),
    a first vent hole (30) in said first opposite wall (38) placing said inlet chamber (20) in fluid communication with atmosphere through said first opposite wall (38),
    said first vent hole (30) being located at said filter housing first end, a second vent hole (32) in said second opposite wall (46) placing said inlet chamber (20) in fluid communication with atmosphere through said second opposite wall (46),
    said second vent hole (32) being located at said filter housing second end,
    said first and second vent holes (30, 32) being covered by respective first and second hydrophobic membranes (34, 36),
    an inlet conduit (10) in fluid communication with said inlet chamber (20) at said filter housing first end, and
    an outlet conduit (14) in fluid communication with said outlet chamber (22) at said filter housing second end.

2. The filter as defined in claim 1 wherein the housing is of a predetermined width adjacent said first vent hole (30) and adjacent said second vent hole (32); and at least one of the hydrophobic membranes (34, 36) extends substantially over the predetermined filter housing width adjacent to at least one of the first vent hole (30) and the second vent hole (32).

3. The filter as defined in claim 1 wherein said filter housing first end is an upper end of the filter housing when the filter is vertically oriented.

4. The filter as defined in claim 1 wherein the filter housing is of triangular configuration defined by a vertex and a base, and said outlet conduit (14) is located at said vertex.

5. The filter as defined in claim 1 including one of a supporting lug (50) and supporting ribs are provided at one of said first and second walls (38, 46).

6. The filter as defined in claim 4 wherein the triangular shape of the filter housing is asymmetrical.

7. The filter as defined in claim 2 wherein said first hydrophobic membrane (34) extends substantially over the predetermined filter housing width adjacent to said first vent hole (30).

8. The filter as defined in claim 2 wherein said second hydrophobic membrane (36) extends substantially over the predetermined filter housing width adjacent to said second vent hole (32).

9. The filter as defined in claim 7 wherein said second hydrophobic membrane (36) extends substantially over the predetermined filter housing width adjacent to said second vent hole (32).

10. The filter as defined in claim 1 wherein said inlet chamber (20) and said outlet chamber (22) are each of a triangular configuration disposed in opposing relationship to each other, said hydrophilic filter (18) is of a triangular configuration, and said triangular hydrophilic filter (18) is disposed in substantially geometrically matching relationship to and between the triangular inlet and outlet chambers.

11. A filter for medical fluids comprising:
    a filter housing including first and second ends and opposite walls (38, 46) defining opposite sides of said filter housing, a hydrophilic filter (18) between said opposite walls (38, 46), a first (38) of said opposite walls (38, 46) and said hydrophilic filter (18) defining an inlet chamber (20), a second (46) of said opposite walls (38, 46) and said hydrophilic filter (18) defining an outlet chamber (22), a first vent hole (30) in said first opposite wall (38) opposite to the hydrophilic filter (18) opening to atmosphere in a first direction, said first vent hole (30) being located at said filter housing first end, a second vent hole (32) in said second opposite wall (46) opposite to the hydrophilic filter (18) opening to atmosphere in a second direction opposite to said first direction, said second vent hole (32) being located at said filter housing second end, said first and second vent holes (30, 32) being covered by respective first and second hydrophobic membranes (34, 36), an inlet conduit (10) in fluid communication with said inlet chamber (20) at said filter housing first end, an outlet conduit (14) in fluid communication with said outlet chamber (22) at said filter housing second end, said filter housing is of a triangular shape, said housing being of a predetermined width adjacent said first vent hole (30) and adjacent said second vent hole (32), and at least one of the hydrophobic membranes (34, 36) extends substantially over the predetermined filter housing width adjacent to the first vent hole (30) and the second vent hole (32).

12. The filter as defined in claim 11 wherein said triangular shaped filter housing includes an apex and an opposite base disposed respectively adjacent said second and first vent holes (30, 32).

13. The filter as defined in claim 11 wherein said first hydrophobic membrane (34) extends substantially over the predetermined filter housing width adjacent to said first vent hole (30).

14. The filter as defined in claim 11 wherein said second hydrophobic membrane (36) extends substantially over the predetermined filter housing width adjacent to said second vent hole (32).

15. The filter as defined in claim 13 wherein said second hydrophobic membrane (36) extends substantially over the predetermined filter housing width adjacent to said second vent hole (32).

16. The filter as defined in claim 11 wherein said inlet chamber (20) and said outlet chamber (22) are each of a triangular configuration disposed in opposing relationship to each other, said hydrophilic filter (18) is of a triangular configuration, and said triangular hydrophilic filter (18) is disposed in substantially geometrically matching relationship to and between the triangular inlet and outlet chambers.

* * * * *